(12) United States Patent
Park et al.

(10) Patent No.: US 7,435,593 B2
(45) Date of Patent: Oct. 14, 2008

(54) HYBRID BIO ACTUATOR AND METHOD OF MANUFACTURING THE SAME USING 3-DIMENSIONAL MICRO MOLDING ALIGNER

(75) Inventors: Suk-ho Park, Seoul (KR); Jin-seok Kim, Seoul (KR); Jung-yul Park, Seoul (KR); Duk-moon Rho, Seoul (KR); Byung-kyu Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 20 days.

(21) Appl. No.: 11/512,356

(22) Filed: Aug. 30, 2006

(65) Prior Publication Data
US 2007/0141647 A1  Jun. 21, 2007

(30) Foreign Application Priority Data
Dec. 20, 2005  (KR) ............... 10-2005-0126160

(51) Int. Cl.
*B29C 43/36* (2006.01)
(52) U.S. Cl. ............... 435/396; 425/193; 425/406; 425/450.1; 425/451.9; 435/402; 264/238; 264/325; 264/338
(58) Field of Classification Search ............... 425/150, 425/193, 195, 406, 450.1, 451.9, 318; 424/93.7; 435/396, 402, 366; 264/238, 325, 338
See application file for complete search history.

(56) References Cited

U.S. PATENT DOCUMENTS

| | | | | |
|---|---|---|---|---|
| 220,172 | A | * | 9/1879 | Rathsam .................. 425/318 |
| 4,457,684 | A | * | 7/1984 | Gram .................. 425/451.9 |
| 6,679,698 | B2 | * | 1/2004 | Abe et al. ................ 425/153 |

* cited by examiner

*Primary Examiner*—Robert B Davis
(74) *Attorney, Agent, or Firm*—McDermott Will & Emery LLP

(57) ABSTRACT

A hybrid bio actuator and a manufacturing method thereof using a 3-dimensional micro molding aligning apparatus are provided. The manufacturing method has the steps of: 3-dimensionally forming an actuator body with polymer using the micro molding aligning apparatus; and transplanting and cultivating the muscular cell onto the actuator body. The step of forming the actuator body comprise: preparing the upper and lower half molds corresponding to an outer contour of the actuator; installing, on the mold plate unit, the upper and lower half molds opposite to each other and placing a mass of polymer above the lower half mold; aligning the lower half mold with the upper half mold using the aligner unit; pressing the mold plate unit using the clamp unit; solidifying the polymer; and removing the solidified polymer, thereby providing the hybrid bio actuator made of a biomaterial compatible with the human body and capable of operating without a separate battery or external energy source.

22 Claims, 23 Drawing Sheets

HYBRID BIO ACTUATOR AND METHOD OF MANUFACTURING THE SAME USING 3-DIMENSIONAL MICRO MOLDING ALIGNER

CROSS-REFERENCE TO RELATED APPLICATION

This application claims all benefits of Korean Patent Application No. 10-2005-126160, filed on Dec. 20, 2005 in the Korean Intellectual Property Office, the disclosures of which is incorporated herein by reference.

BACKGROUND OF THE INVENTION

1. Field of the Invention

The present invention relates to a hybrid bio actuator and a method of manufacturing the same using a 3-dimensional micro molding aligner, and more particularly to a method of manufacturing an actuator, which prepares an actuator body made of polydimethylsiloxane (PDMS) using a 3-dimensional micro molding aligner, and cultivates the muscular cells on the PDMS actuator to manufacture the actuator, and a hybrid bio actuator manufactured by the method.

2. Description of the Prior Art

A hybrid bio actuator is one of the results of the recently noted nano-technology, which actuator has a very small size in micrometer unit for general use in curing the interior of the human body.

However, since the bio actuator is very small, it is difficult to manufacture the bio actuator. In the prior art, there was generally provided only one half mold so as to mold a bio actuator using the same. However, since the prior method used only one half mold, the bio actuator was constructed at only one side thereof so that it was difficult to mold both sides of the actuator.

Meanwhile, the metallic material of the prior actuator body may cause rejection symptoms to the interior of the human body so it is improper to use. In addition, the actuator requires energy source to operate, but it is difficult for the actuator to be supplied with the energy source from exterior or to be provided with a separate battery and so on while maintaining very small size. Further, if the muscular cells are used as the energy source, it is troublesome to transplant, onto the actuator body, the muscular cells that have been cultivated in the exterior, so that it is true that the mass production of a bio actuator is difficult.

SUMMARY OF THE INVENTION

Accordingly, the present invention has been made to solve the above-mentioned problems occurring in the prior art, and an object of the present invention is to provide a 3-dimensional micro molding aligning apparatus capable of forming constructions on both sides of a bio actuator.

Another object of the present invention is to provide a bio actuator operable without a separate battery or external energy source and made of a biomaterial compatible with the interior of the human body, and a manufacturing method thereof.

In order to accomplish the above objects, there is provided a 3-dimensional micro molding aligning apparatus for 3-dimensionally molding a hybrid bio actuator body, the apparatus comprising: a base having thereon a plurality of support legs; a mold plate unit supported by the support legs and having upper and lower half molds corresponding to an outer contour of the bio actuator and installed opposite to each other; an aligner unit for aligning the lower half mold with the upper half mold; and a clamp unit for pressing the upper half mold of the mold plate unit toward the lower half mold.

In an another aspect of the present invention, there is provided a method for manufacturing a hybrid bio actuator using a 3-dimensional micro molding aligning apparatus, the method comprising the steps of: 3-dimensionally forming an actuator body with polymer using the micro molding aligning apparatus; and transplanting a muscular cell onto the actuator body to cultivate the same.

The step of forming the actuator body may comprise: preparing the upper and lower half molds corresponding to an outer contour of the actuator; installing, on the mold plate unit, the upper and lower half molds opposite to each other and placing a mass of polymer above the lower half mold; aligning the lower half mold with the upper half mold using the aligner unit; pressing the mold plate unit using the clamp unit; solidifying the polymer; and removing the solidified polymer.

The step of transplanting and cultivating the muscular cell may comprise: setting the actuator body in a culture vessel; and transplanting the muscular cell onto the actuator body in the culture vessel filled with a culture solution and cultivating the same.

Meanwhile, the hybrid bio actuator manufactured by the above method according to the present invention operates on glucose as an energy source and in which one or more muscular cells are transplanted onto the actuator body so that it can operate with the contraction and relaxation of the muscular cells.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, preferred embodiments of the present invention will be described with reference to the accompanying drawings. A 3-dimensional micro molding aligning apparatus for manufacturing a bio actuator will be first explained, and a manufacturing method of the bio actuator using the apparatus and the bio actuator manufactured by the method will be explained in series.

Figure 1:
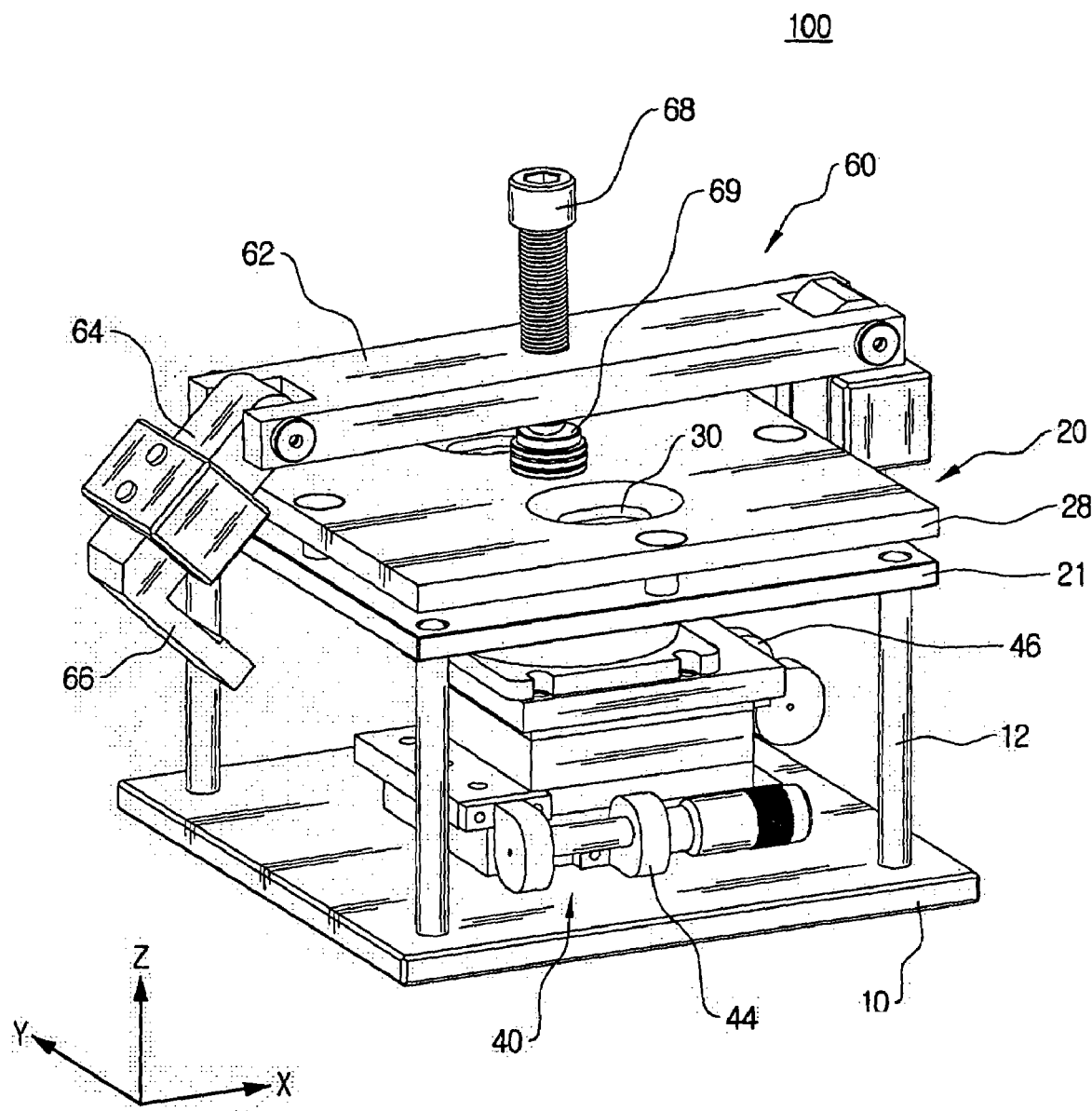
FIG. 1 is a perspective view of a 3-dimensional micro aligning apparatus according to a preferred embodiment of the present invention.
Figure 2:
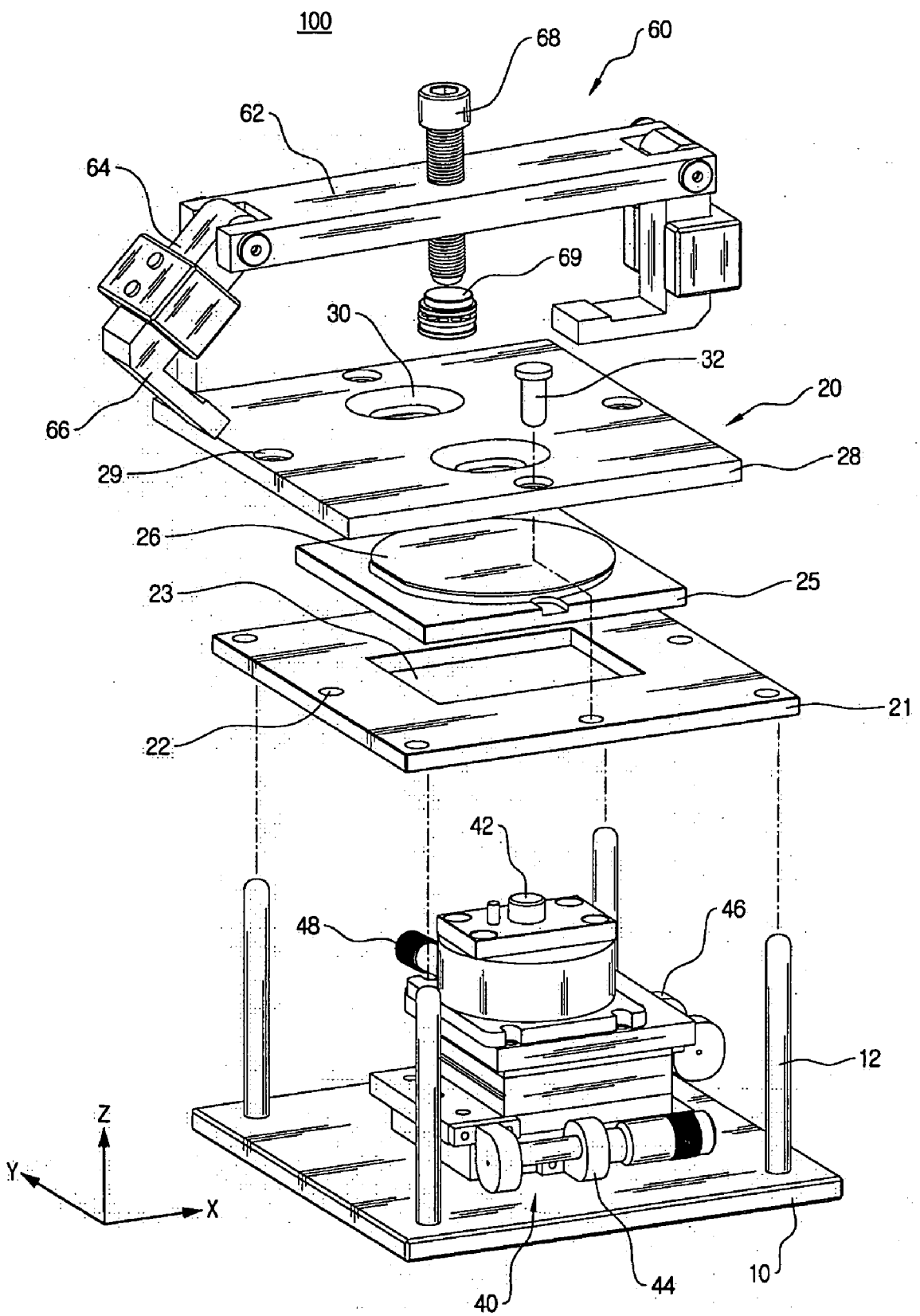
FIG. 2 is an exploded perspective view of FIG. 1.

FIG. 1 is a perspective view of a 3-dimensional micro aligning apparatus according to a preferred embodiment of the present invention, and FIG. 2 is an exploded perspective view of FIG. 1.

Referring to FIGS. 1 and 2, the 3-dimensional micro molding aligning apparatus 100 includes a base 10 on which various constituent elements to be explained later are installed. The base 10 has a plurality of support legs 12 extending vertically therefrom. Preferably, four support legs 12, as shown in FIGS. 1 and 2, are installed on the corner portions of the base 10 to firmly support a following mold plate unit 20.

The mold plate unit 20 is fixed to the distal ends of the support legs 12. Upper and lower half molds (80 and 70 in FIG. 13) corresponding to an outer contour of a bio actuator are installed opposite to each other on the mold plate unit 20. Specifically, the mold plate unit 20 includes a lower mold plate 21 fixedly supported by the support legs 12, a middle mold plate 25 movably positioned above the lower mold plate 21, and an upper mold plate 28 positioned above the middle mold plate 25.

The lower mold plate 21 enables the middle mold plate 25 to move along the upper portion thereof, and serves to support the whole of the mold plate unit 20. The lower mold plate 21 has a center through-hole 23, through which an aligner unit 40 to be explained later is connected with the middle mold plate 25. The through-hole 23 has a proper size, preferably, smaller than the middle mold plate 25 such that the middle mold plate 25 above the lower mold plate 21 does not pass through the through-hole.

The middle mold plate 25 is movably positioned above the lower mold plate 21, as described above. A mold fixture portion 26 is provided on the upper portion of the middle mold plate 25 to fix the lower half mold 70. Since the lower half mold 70 is detachably fixed to the fixture portion 26, an operator fixes various lower half molds 70 to the fixture portion 26, thereby forming a shape of a bio actuator desired to fabricate.

The upper mold plate 28 is positioned above the middle mold plate 25, and as is not shown in the drawings, a fixture portion is provided at the center portion of under surface of the upper mold plate so as to fix the upper half mold thereto. Like the lower half mold 70, the upper half mold 80 is detachably fixed to the fixture portion of the upper mold plate 28. Accordingly, the upper and lower half molds 80 and 70 of the upper and lower mold plates 28 and 25, respectively, are installed opposite to each other.

Meanwhile, a plurality of through-holes 29 is formed near the edges of the upper mold plate 28, and through-holes 22 are also formed at positions of the lower mold plate 21 corresponding to the former through-holes. The upper and lower mold plates 28 and 21 are fixed by pins 32 passing through both the through-holes 29 and 22 so that they cannot move horizontally, but move vertically. That is, the upper mold plate 28 cannot move horizontally to the lower mold plate 21 due to the pins 32, but it can move vertically along the pins 32. Such construction makes it possible for the upper mold plate 28 to move vertically toward the lower mold plate 21 along the pins 32 when it is pressed by a clamp unit 40 to be explained later.

In a preferred embodiment, one or more viewing windows 30 are provided at proper position of the upper mold plate 28, and the upper half mold 80 fixed under the upper mold plate 28 is made of glass. Thus, an operator can observe the upper and lower half molds 80 and 70 through the viewing window 30 using a microscope 34 (See FIG. 13) so as to check an aligned state of the upper and lower half molds 80 and 70.

The aligner unit 40 is positioned on the base 10 so as to slightly move and align the lower half mold 70 relative to the upper half mold 80. Particularly, the aligner unit 40 includes a connection member 42 connected with the middle mold plate 25 through the through-hole 23 of the lower mold plate 21 to interwork therewith, an X-directional aligner 44 for moving the connection member 42 in X-direction, a Y-directional aligner 46 for moving the connection member 42 in Y-direction, and a rotary aligner 48 for rotating the connection member 42 about an Z-axis.

The connection member 42 of the aligner unit 40 can take X and Y-direction straight line motions by the X and Y-directional aligners 44 and 46, and a Z-direction rotational motion by the rotary aligner 48. Accordingly, an operator can align the upper and lower half molds 80 and 70 with each other through moving the connection member 42 of the aligner unit 40 after he observes the aligning state of the half molds through the viewing window 30 of the upper mold plate 28, using the microscope 34. In this way, the connection member 42 can slightly move and control the middle mold plate 25 interconnected with the connection member 42 and the lower half mold 70 fixed to the fixture portion 26 of the middle mold plate 25. Thus, an operator slightly moves and controls the lower half mold 70 fixed to the middle mold plate 25 using the aligner unit 40 to thus align the same with the upper half mold 80.

In a preferred embodiment, it is employed M433, M423 or M481-A of Newport Company as the aligner unit 40. The aligner units have been developed and known in the art, so the detailed explanation thereof will be omitted.

The clamp unit 60 is selectively fixed to the upper portion of the mold plate unit 20 so as to press the upper mold plate 28 toward the middle and lower mold plates 25 and 21, thereby pressing the upper half mold 80 toward the lower half mold 70.

Particularly, the clamp unit 60 includes a body portion 62 in length. The body portion 62 preferably has a length corresponding to the mold plate unit 20 so as to be easily fixed thereto.

Pivot legs 64 are pivotably connected to both ends of the body portion 62. The pivot leg 64 has at its distal end an extension 66 extending vertically. When the pivot legs 64 are positioned vertically to the body portion 62 and a pressing bolt 68 presses the upper mold plate 28, the extension 66 becomes to be positioned under the mold plate unit 20, i.e., the lower mold plate 21, to support the mold plate unit 20.

The pressing bolt 68 presses the upper mold plate 28 toward the middle and lower mold plates 25 and 21, passing through the body portion 62, thereby implementing the molding in which the upper half mold 80 of the upper mold plate 28 is pressed toward the lower half mold 70 of the middle mold plate 25.

Meanwhile, an anti-deformation member 69 is provided near the end of the pressing bolt 68 where the pressing bolt brings into contact with the upper mold plate 28. Upon pressing of the pressing bolt 68, the anti-deformation member 69 prevents the pressing bolt 68 from directly contacting the upper mold plate 28 to cause a deformation. The anti-deformation member 69 may be used in many forms, such as a bearing as shown in FIG. 2.

Figure 3:
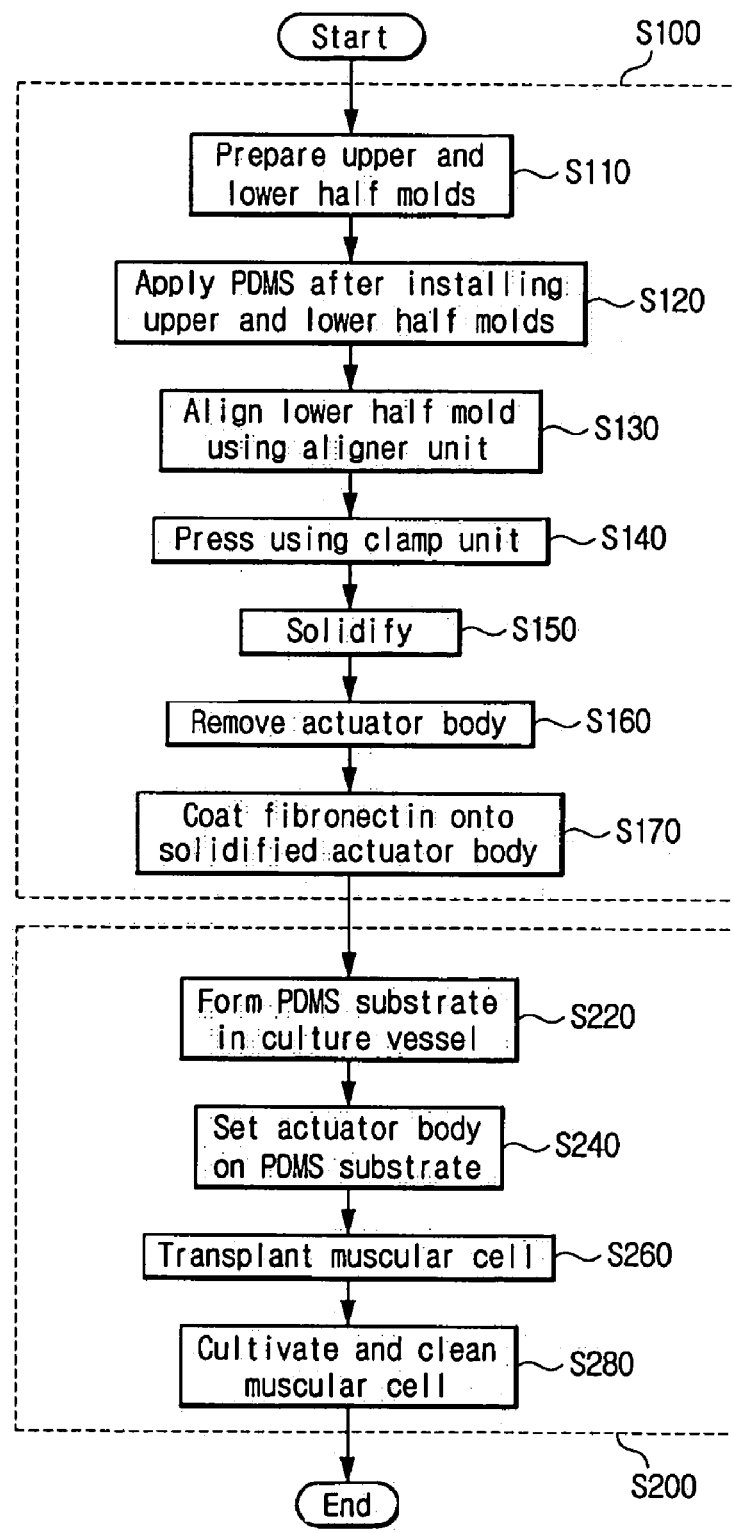
FIG. 3 is a flow chart illustrating a process of manufacturing a hybrid bio actuator according to the present invention.

FIG. 3 is a flow chart of a method of manufacturing a bio actuator according to the present invention. Hereinafter, a method of manufacturing a bio actuator using the above-mentioned 3-dimensional micro molding aligning apparatus 100 will be described.

As shown in FIG. 3, the manufacturing method for bio actuator includes the main steps of preparing an actuator body with polydimethylsiloxane (PDMS) (S100), and transplanting and cultivating a muscular cell onto the actuator body (S200).

The bio actuator is manufactured in a very small size for general use in operating in the interior of the human body, so that the actuator body is generally made of harmless PDMS that does not cause a rejection to the organs in the human body. The muscular cell (e.g., myocardial cell) is cultivated after it is transplanted onto the actuator, which is because the method of the present invention can selectively transplant the muscular cell onto only the bio actuator.

Particularly, the step S100 includes: preparing the upper and lower half molds 80 and 70 (FIG. 13) corresponding to an outer contour of the actuator (S110); installing the prepared upper and lower half molds 80 and 70 opposite to each other on the mold plate unit 20 (FIG. 2) and applying PDMS 2 (FIG. 13) on the lower half mold 70 (S120); aligning the lower half mold 70 with the upper half mold 80 using the aligner unit 40 (FIG. 2) (S130); pressing with the clamp unit 60 (FIG. 2) (S140); solidifying the PDMS actuator body (S150); removing the solidified actuator body from the molds (S160); and coating the solidified actuator body with fibronectin (S170)

The process of the manufacturing method of the bio actuator will now be explained in detail.

First, an operator fabricates the upper and lower half molds corresponding to an outer contour of the bio actuator (S120). FIGS. 4 to 8 show the steps of fabricating the lower half mold 70, and FIGS. 9 to 12 show the steps of fabricating the upper half mold 80.

Figure 4:
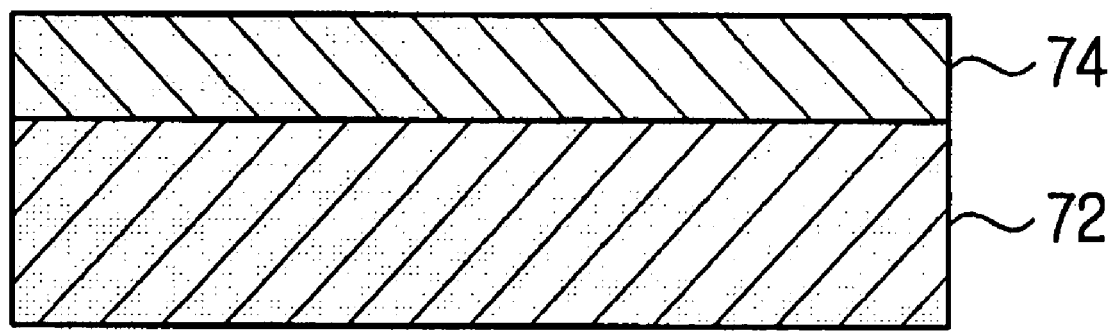
FIGS. 4 to 8 are views illustrating a process of preparing a lower half mold.
Figure 5:
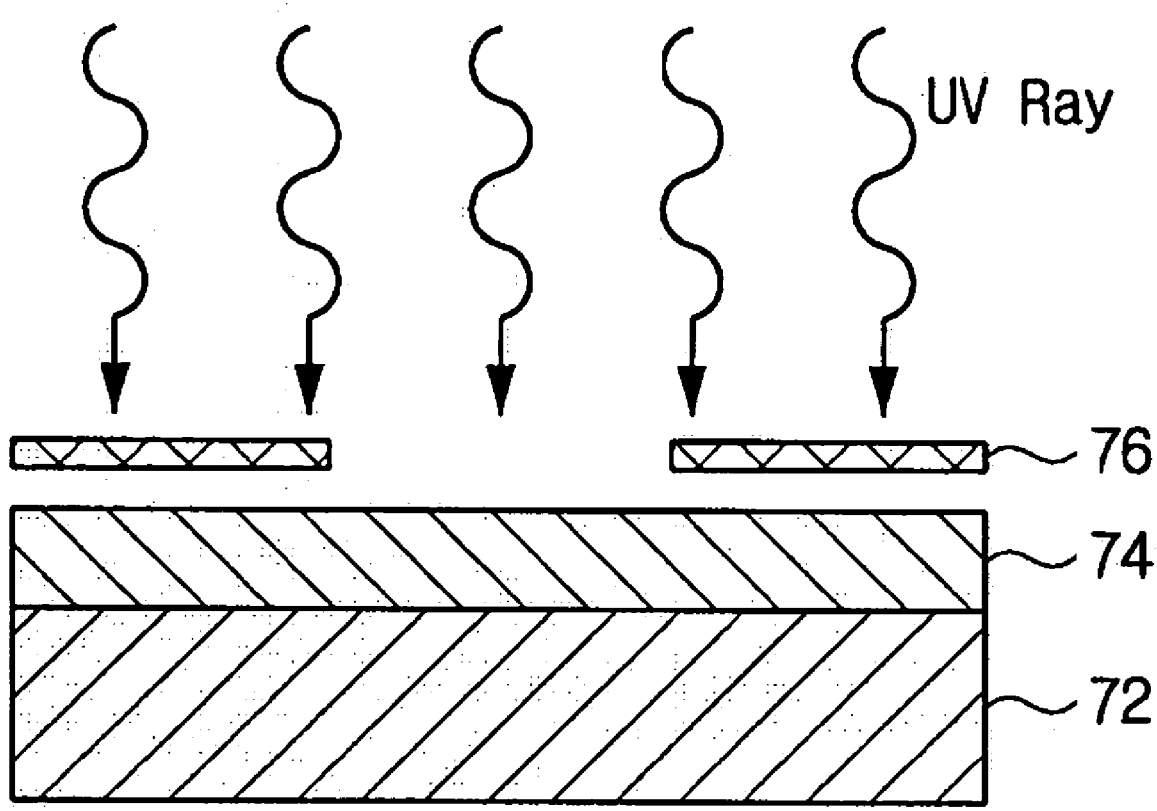
Figure 6:
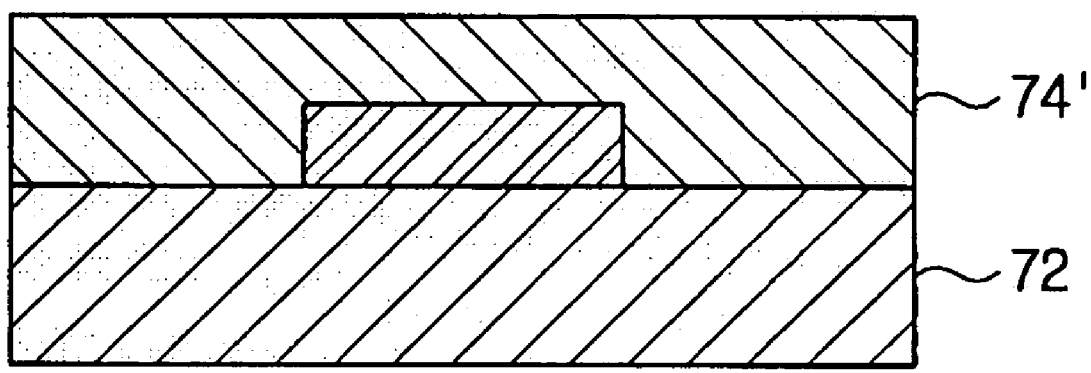
Figure 7:
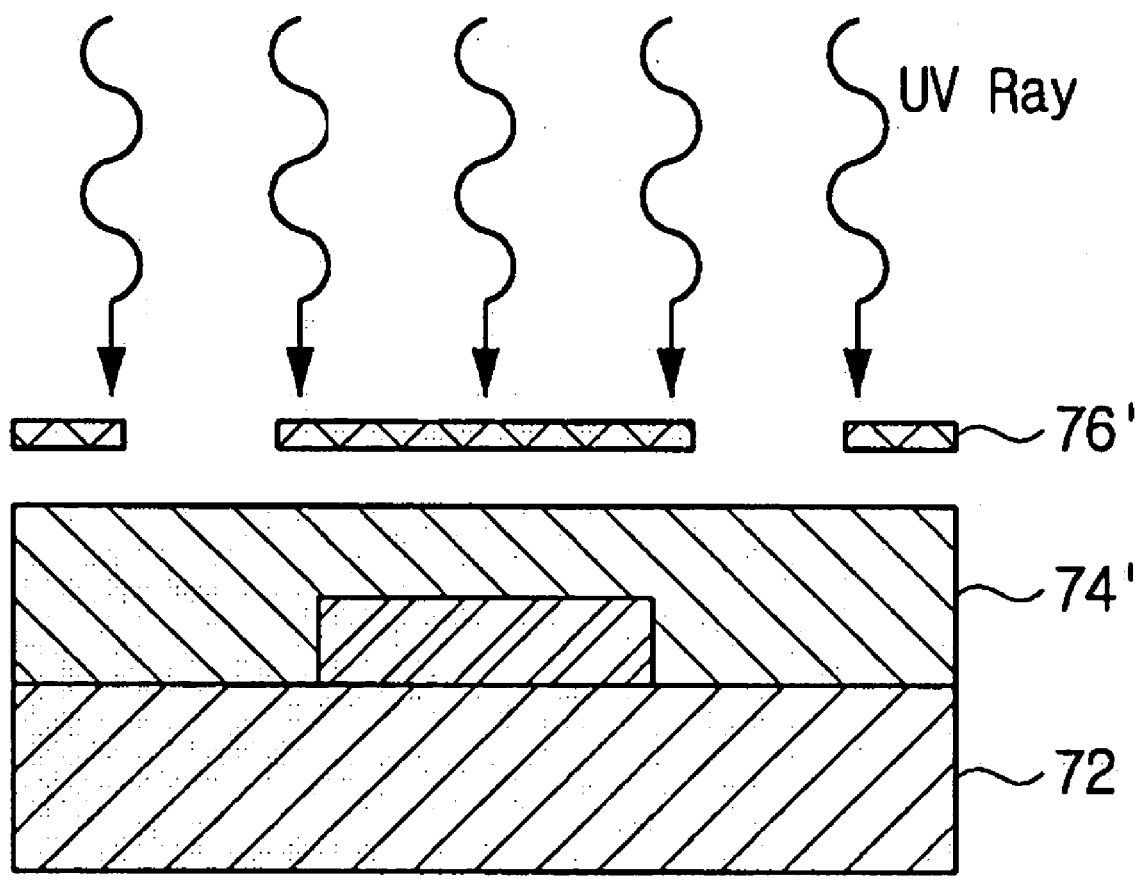
Figure 8:
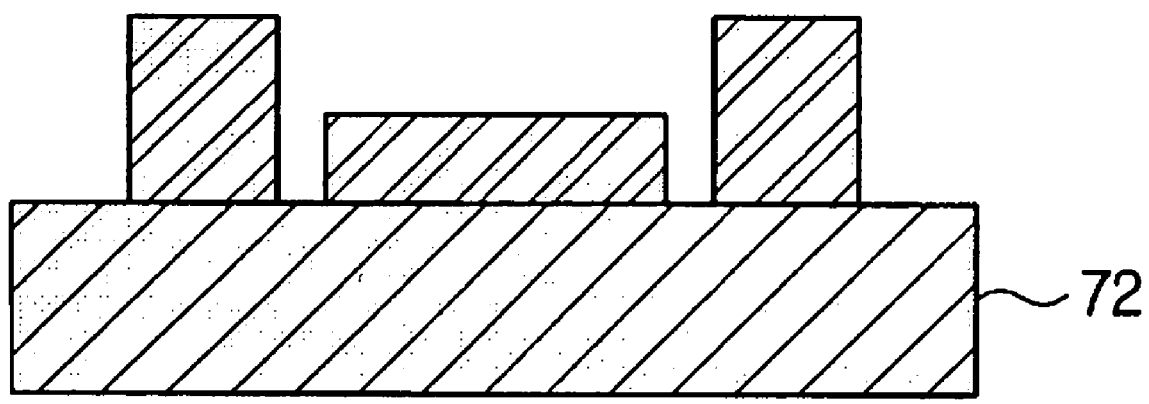

Referring to FIGS. 4 to 8, an operator applies photoresist 74 (e.g., negative photoresist) on a silicon wafer 72 using a spin coater, and pre-bakes it under certain condition of temperature/time (e.g., at 90° C. for 15 min) (See FIG. 4). A photo mask 76 in which channels are designed is placed on the silicon wafer 72 applied with photoresist 74, and an exposure process is implemented thereto for predetermined time (e.g., 20 to 180 sec) (See FIG. 5). The silicon wafer 72 is immersed into a developing solution (e.g., SU-8 solvent) for predetermined time (e.g., 5 min) to develop, and is post-baked under certain condition of temperature/time (e.g., at 90° C. for 15 min) to form the lower half mold 70. If the lower half mold 70 has more complicated construction, it can be formed by repeating the above processes. That is, the resultant silicon wafer 72 is further applied with photoresist 74' to pre-bake (See FIG. 6), a photo mask 76' in which different channels from the photo mask 76 are designed is placed on the former silicon wafer to expose the same to ultraviolet ray for certain time (See FIG. 7), and the resultant silicon wafer is immersed into a developing solution to develop and post-baked to form a lower half mold. FIG. 8 shows the lower half mold 70 fabricated by repeating the above process. Referring to FIG. 8, it can be seen that more complicated lower half mold is formed through the above process.

Figure 9:
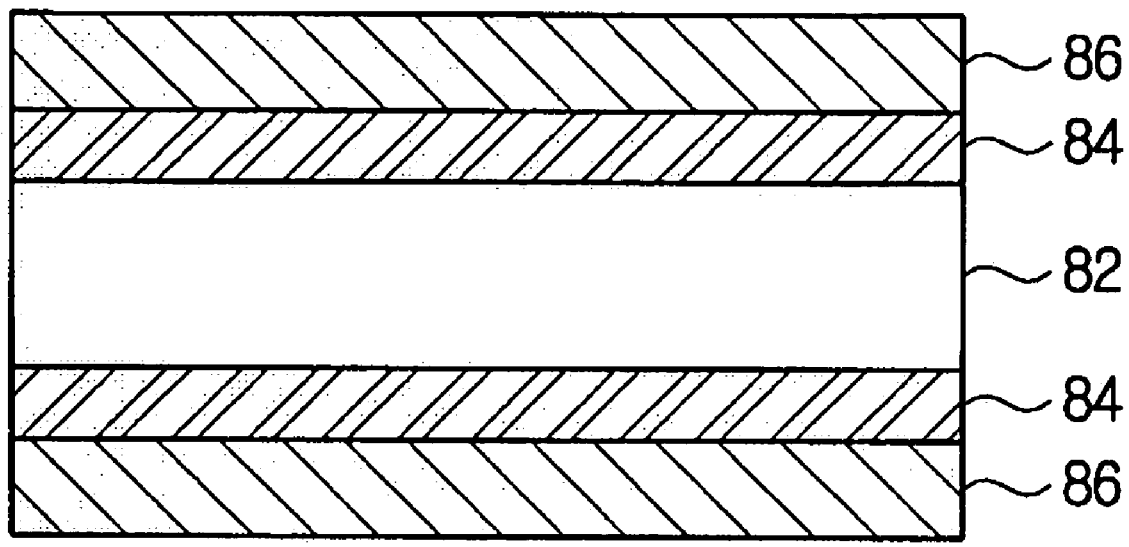
FIGS. 9 to 12 are views illustrating a process of preparing an upper half mold.
Figure 10:
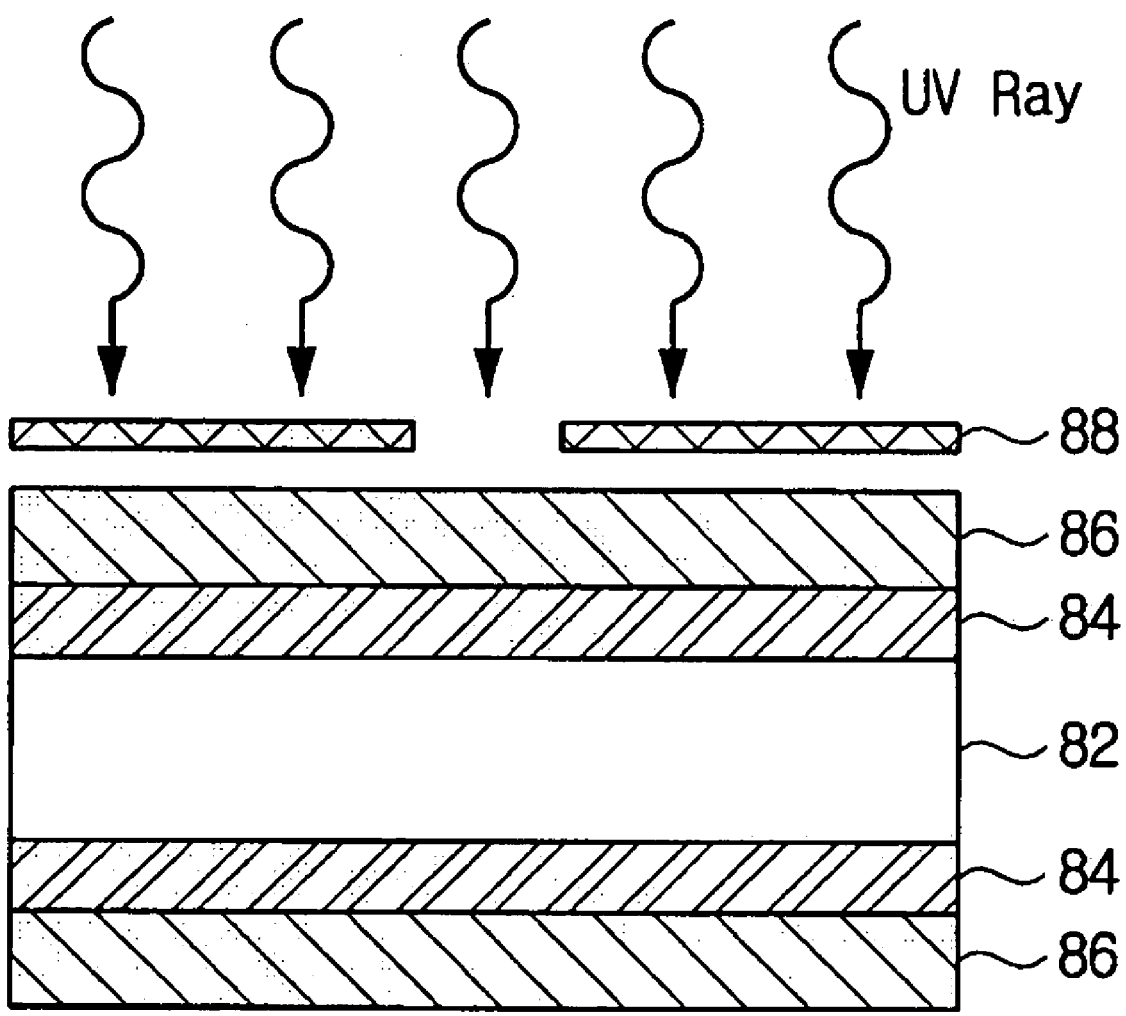
Figure 11:
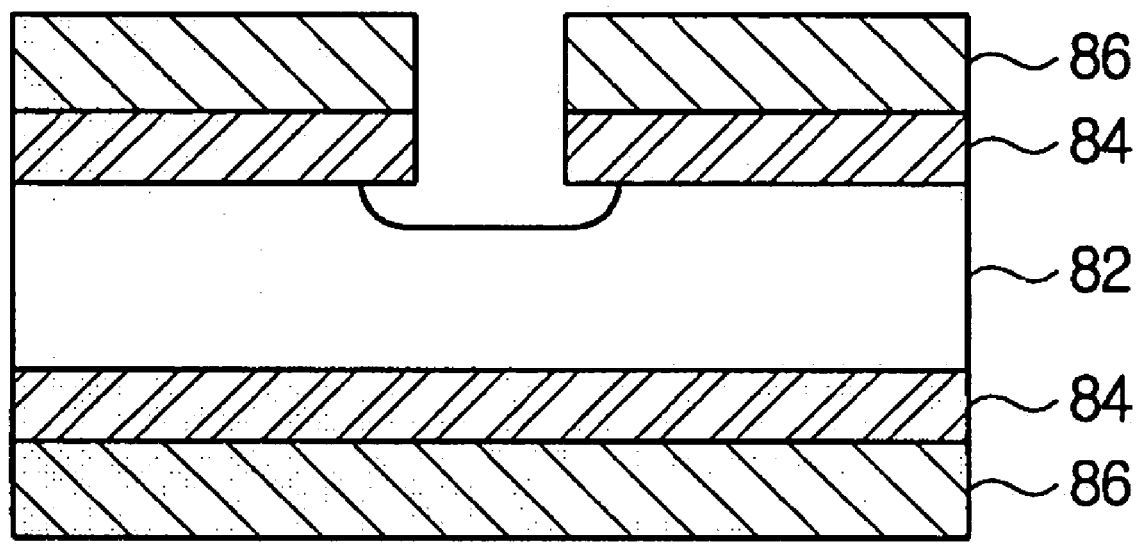
Figure 12:
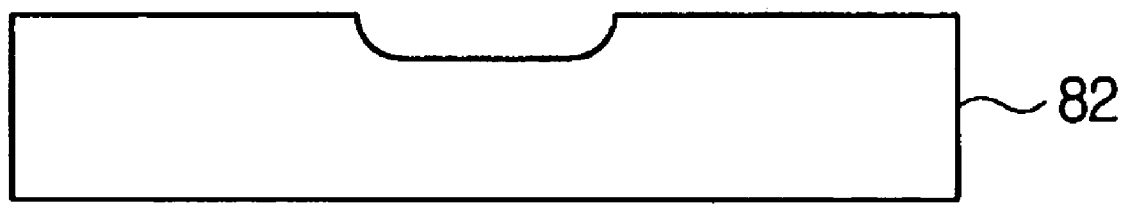

Referring to FIGS. 9 to 12, an operator applies photoresist 86 on both sides of a glass plate 82 coated with Cr/Au 84, and pre-bakes it (FIG. 9). A photo mask 86 in which channels are designed is placed on the applied photoresist 86, an exposure process is implemented thereto for predetermined time (See FIG. 10), and the glass plate is etched (FIG. 11) to form the upper half mold 80 of glass plate. FIG. 12 shows the upper half mold 80 fabricated by the process.

Figure 13:
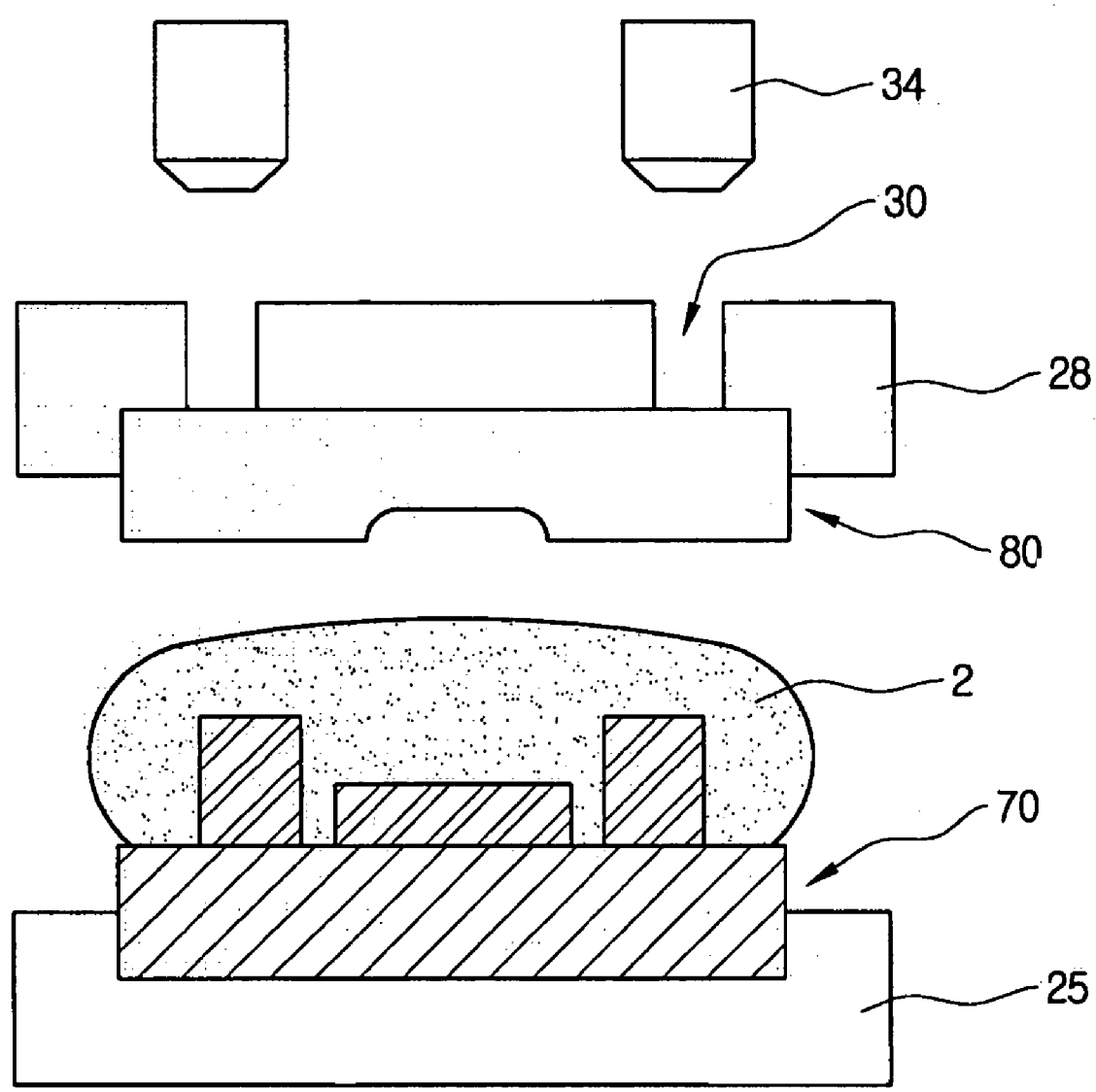
FIG. 13 is a schematic view of a 3-dimensional micro molding aligning apparatus which fabricates a hybrid bio actuator using the upper and lower half molds.

After being prepared, the upper and lower half molds 80 and 70 are installed opposite to each other on the mold plate unit 28 (FIG. 2) of the micro molding aligning apparatus 100 (FIG. 2). Specifically, the upper half mold 80 is installed on the fixture portion (not shown) formed under the upper mold plate 28 (FIG. 2), and the lower half mold 70 on the fixture portion 26 formed on the middle mold plate 25 (FIG. 2). The middle mold plate 25 is positioned above the lower mold plate 21, and the upper and lower mold plates 28 and 21 are fixed using the pins 32. FIG. 13 schematically shows the aligning apparatus 100 with the upper and lower half molds 80 and 70 installed thereon opposite to each other. After the upper and lower half molds 80 and 70 are arranged, polymer composing the actuator body, preferably, PDMS 2 (FIG. 13), is positioned on the lower half mold 70 (S120).

Then, an operator slightly moves and aligns the lower half mold 70 using the aligner unit 40 connected to the mold plate unit 20 (S130). Particularly, as shown in FIG. 13, the operator observes an aligned state of the upper and lower half molds 80 and 70 through the viewing window 30 of the upper mold plate 28, using the microscope 34. In the preferred embodiment, the upper half mold 80 is made of glass so that the operator can observe the aligned state of the upper and lower half molds 80 and 70 through the viewing window 30. If the upper and lower half molds are aligned off, the operator controls the aligner unit 40 connected with the middle mold plate 25 through the hole 23 of the lower mold plate 21 to slightly move the middle mold plate 25 to control the aligned state. That is, the operator can rearrange the aligned state of the lower half mold 70 by moving the middle mold plate 25 in X or Y direction, or rotating it about Z-axis, using the X, Y-directional, or rotary aligner 44, 46, or 48 (FIG. 2) of the aligner unit 40 (FIG. 2).

After the rearrangement in the aligned state of the upper and lower half molds 80 and 70 using the aligner unit 40, the operator presses the mold plate unit 20 using the clamp unit 60 (FIG. 2) (S140). The operator positions the body portion 62 (FIG. 2) of the clamp unit 60 above the upper mold plate 28, and rotates the pivot legs 64 pivotably connected to both ends of the body portion 62 vertically to the body portion 62. Then, the extension 66 extending vertically to the end of the pivot leg 64 becomes to naturally support the lower portion of the lower mold plate 21. The operator rotates the pressing bolt 68 passing through the body portion 62 to press the upper mold plate 28, which in turn becomes close contact with the middle mold plate 25 while moving vertically along the pin 32. Upon pressing by the pressing bolt 68, the anti-deformation member 69 such as bearing is connected to the end of the pressing bolt 68 in order to prevent the deformation of the upper mold plate 28.

As the upper mold plate 28 becomes close contact with the middle mold plate 25, the upper half mold 80 fixed to the upper mold plate 28 becomes close contact with the lower half mold 70 fixed to the middle mold plate 25. Accordingly, as shown in FIG. 13, PDMS 2 applied onto the lower half mold can be molded in a desired shape by the upper and lower half molds 80 and 70.

After pressing with the camp unit 60, the operator removes the mold plate unit 20 from the support legs 12 of the base 10, and puts the mold plate unit 20 inn an oven (not shown) to solidify the same under certain condition of temperature (e.g., 120° C.)/time (e.g., 2 hours) (S150).

Then, the solidified actuator body is removed from the lower half mold 70, i.e., the silicon wafer(S160). In this case, before the application of PDMS to the lower half mold 70 composed of silicon wafer, if a tridecafluoro-1,1,2,2-tetrahydrooctyl-1-trichlorosilane solution is pre-coated onto the lower half mold 70, i.e., silicon wafer, to form silane group, or otherwise, $C_4F_8$ in plasma is coated onto the silicon wafer using a deep RIE, the PDMS actuator body can be easily removed from the lower half mold 70.

Figure 14:
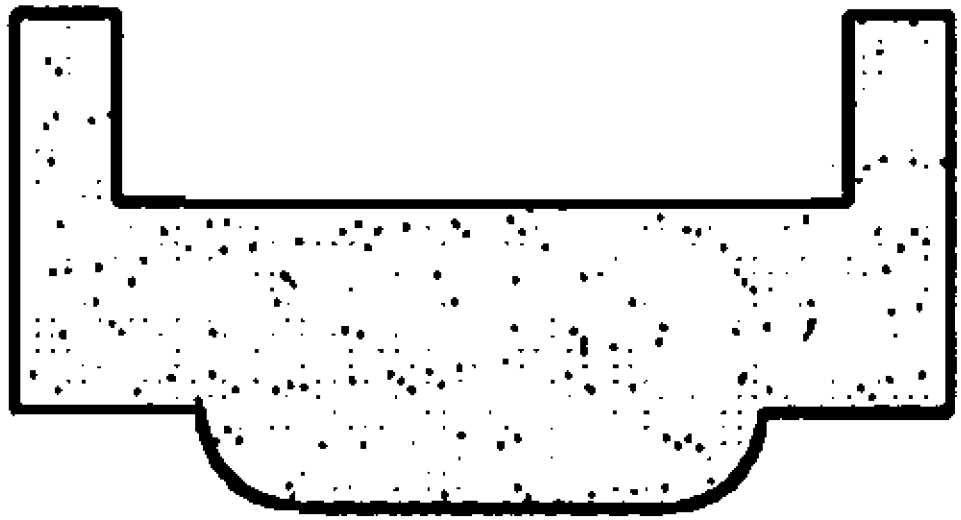
FIG. 14 is a front view of a bio actuator body fabricated by the apparatus of FIG. 13.

The solidified PDMS composes the bio actuator body. Further, fibronectin is coated onto a portion of the bio actuator body to improve the adhesion of the muscular cell to be transplanted. Various methods of coating fibronectin may be employed, such as a method in which OH group is formed on the PDMS bio actuator body using $O_2$ plasma, and fibronectin is then coated thereon. FIG. 14 shows an embodiment of the bio actuator body 1 manufactured by the above molding process. It can be seen that the bio actuator body 1 of FIG. 14 corresponds to the outer contour of the upper and lower half molds 80 and 70 as shown in FIG. 13. The present invention can manufacture the 3-dimensional bio actuator body in which constructions are formed on both upper and lower portions thereof.

Meanwhile, now described is the step S200 of transplanting and cultivating the muscular cell onto the actuator body removed from the lower half mold composed of the silicon wafer. The step S200 comprises: forming a substrate in the culture vessel using PDMS (S220); positioning the PDMS removed from the silicon wafer, i.e., the actuator body, on the PDMS substrate (S240); transplanting the muscular cell onto the actuator body (S260); and cultivating and cleaning the muscular cell (S280).

In case of cultivating the muscular cell while placing only the actuator body made of PDMS in the culture vessel, the muscular cell is transplanted onto both the actuator body and the culture vessel, so that it may be difficult to transplant the muscular cell onto only desired portion of the actuator body. To solve this problem, i.e., to transplant the muscular cell onto only desired portion of the actuator body, PDMS is applied in thickness to the culture vessel to form a PDMS substrate, and the PDMS actuator body coated with fibronectin of the present invention is positioned on the PDMS substrate (S240). The muscular cell has a tendency not to be easily transplanted onto PDMS itself not coated with a cell body material such as fibronectin.

Then, the culture vessel in which the PDMS substrate and the actuator body are positioned is filled with a culture solution containing glucose, and a desired muscular cell is introduced into the culture vessel, thereby transplanting the muscular cell onto the actuator body (S260). In this case, since the portion of the actuator body desired to transplant the muscular cell is coated with fibronectin for improvement in a binding force, the muscular cell is transplanted onto only the portion coated with fibronectin.

After the transplantation of the muscular cell onto the actuator body, the muscular cell is cultivated and cleaned (S280). In the course of cultivation, the muscular cell is cultivated on glucose as an energy source in the culture solution. After the cultivation of the muscular cell, the PDMS substrate and the actuator body are cleaned using Hanks' balanced salt solution (HBSS) so that the muscular cell can be bound to only the portion of the actuator body on which collagen is coated.

FIGS. 15 to 20 are views illustrating embodiments of the bio actuator manufactured by the above process.

Figure 15:
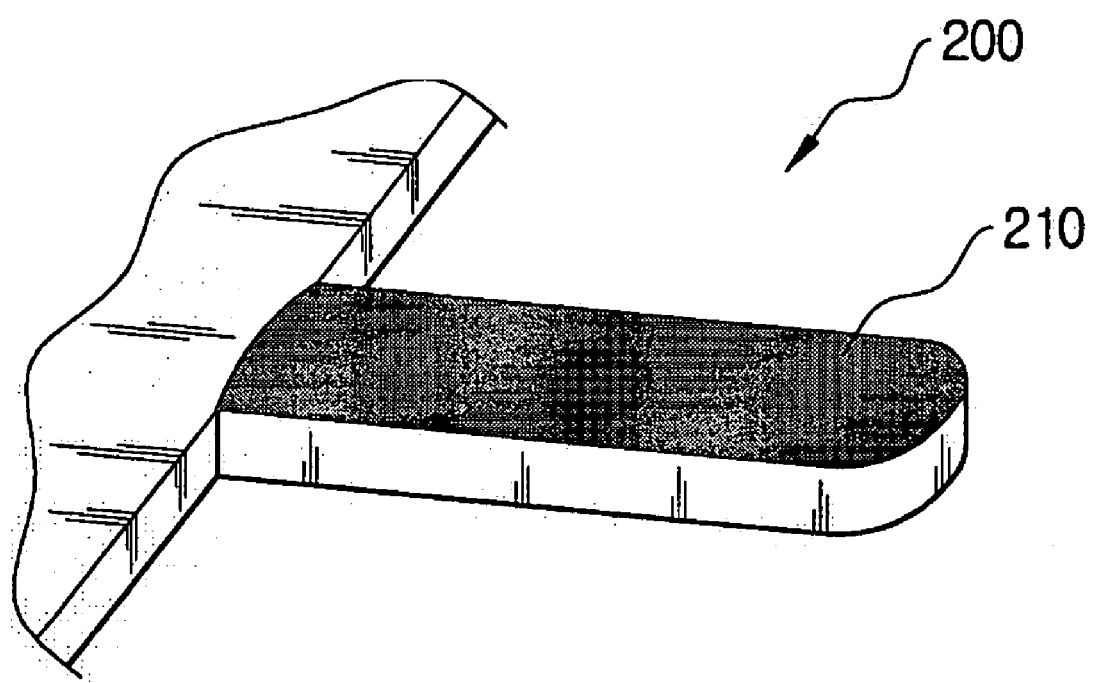
FIG. 15 is a perspective view of a cantilever type actuator.
Figure 16:
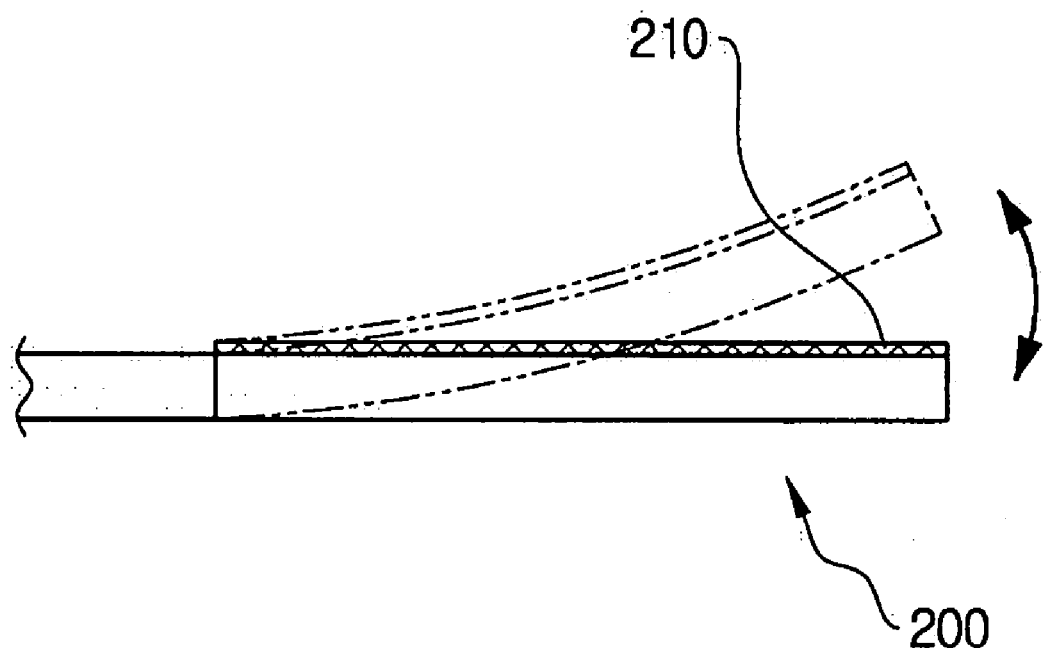
FIG. 16 is a side view showing a movement state of the cantilever type actuator in FIG. 15.
Figure 17:
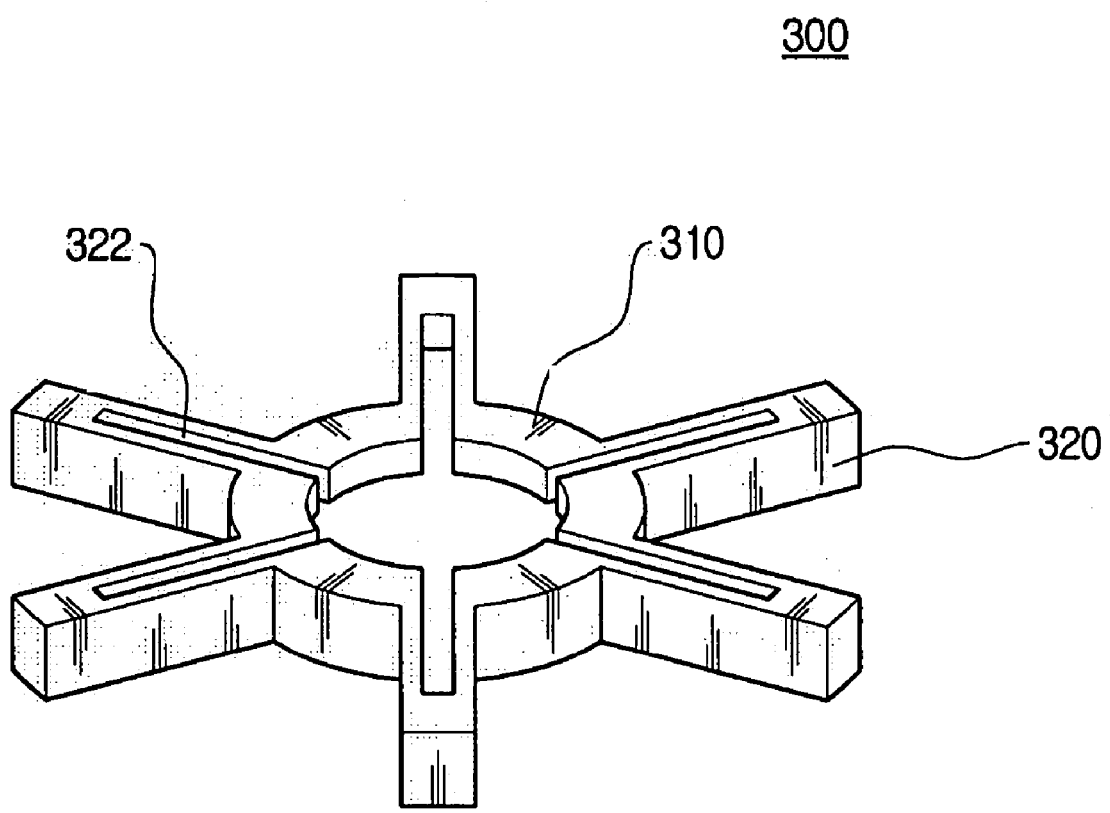
FIG. 17 is a perspective view of a jellyfish type actuator.

FIG. 15 shows a cantilever type actuator. In FIG. 15, the cantilever type actuator is formed with a cantilever 200, on which one or more muscular cells are transplanted and cultivated. The cantilever 200 transplanted with the muscular cells moves in an arrow direction, as shown in FIG. 16, by contraction or relaxation of the muscular cell 210. The cantilever 200 can be used in both performance evaluation of a bio actuator and physical and physiological analysis of a myocardial cell for clinical treatment FIG. 17 shows a jellyfish type actuator. In FIG. 17, the jellyfish type actuator 300 of this embodiment includes a center body 310, and a plurality of wings 320 radially extending from the body 310. The wing 320 has at its upper portion a longitudinal groove 322 in which the muscular cell (not shown) is transplanted to cultivate. Then, when the muscular cell transplanted in the groove 322 of the wing 320 is contracted or relaxed, the wing rotates up and down in the drawing. Such rotation of the wing 320 makes it possible for the jellyfish type actuator 300 to move to a desired position, flowing in a blood vessel of the human body.

Figure 18:
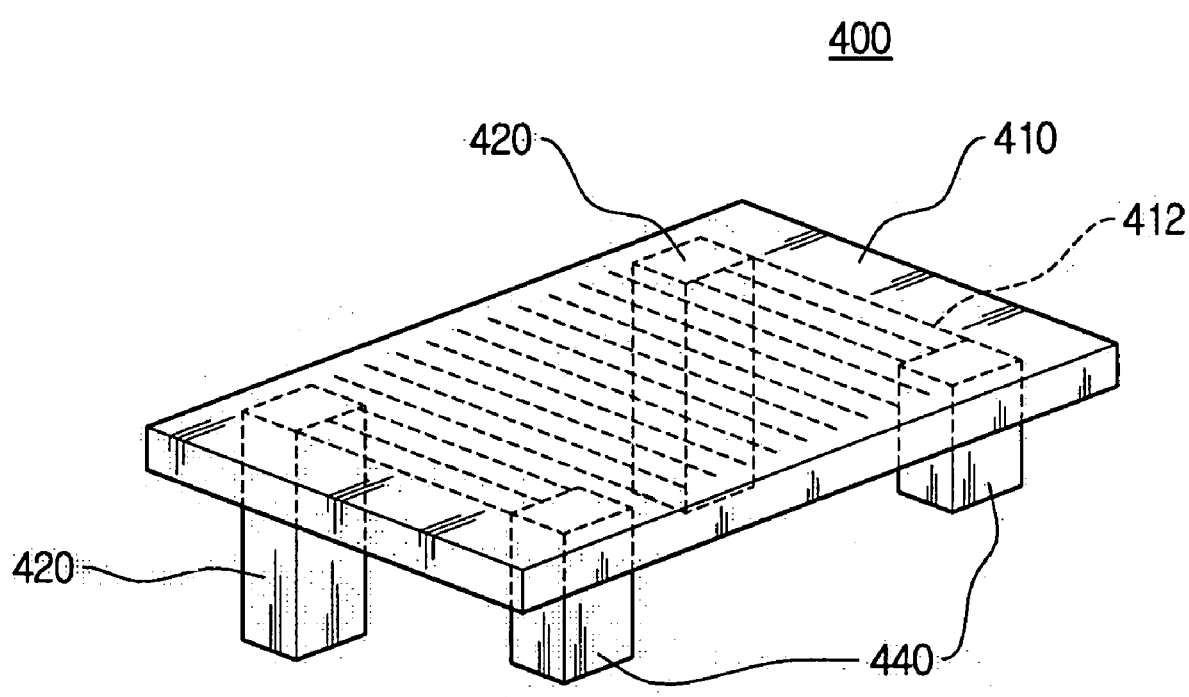
FIG. 18 is a perspective view of a moving actuator.

FIG. 18 shows a moving actuator 400 different from the above embodiments.

Referring to FIG. 18, the actuator of this embodiment includes a body 410 having an under groove 412, and four legs 420 and 440 extending under the body 410. Herein, the four legs 420 and 440 have different length by one pair. The pair of legs 420 vertically to the groove 412 under the body 410 has a longer length than the other pair of legs 440. The difference between lengths is a source of moving the actuator, and is described later in detail. The muscular cell is transplanted onto the under groove 412 of the body 410.

Figure 19:
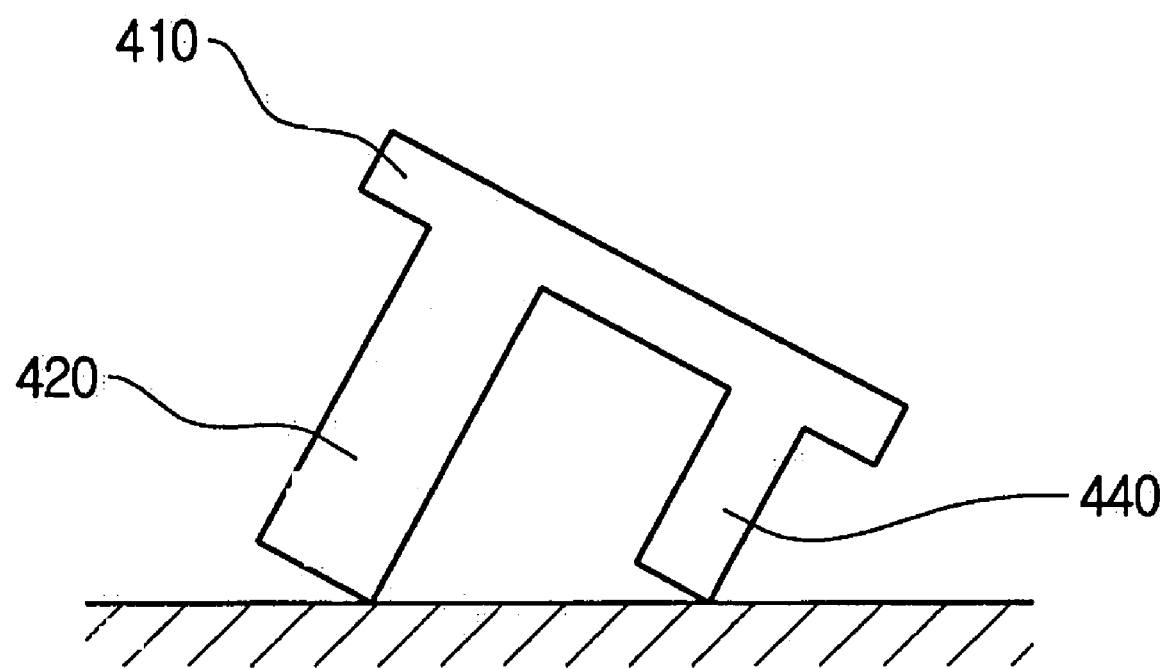
FIG. 19 is a side view showing a state that the moving actuator in FIG. 18 is inclined to a bottom.
Figure 20:
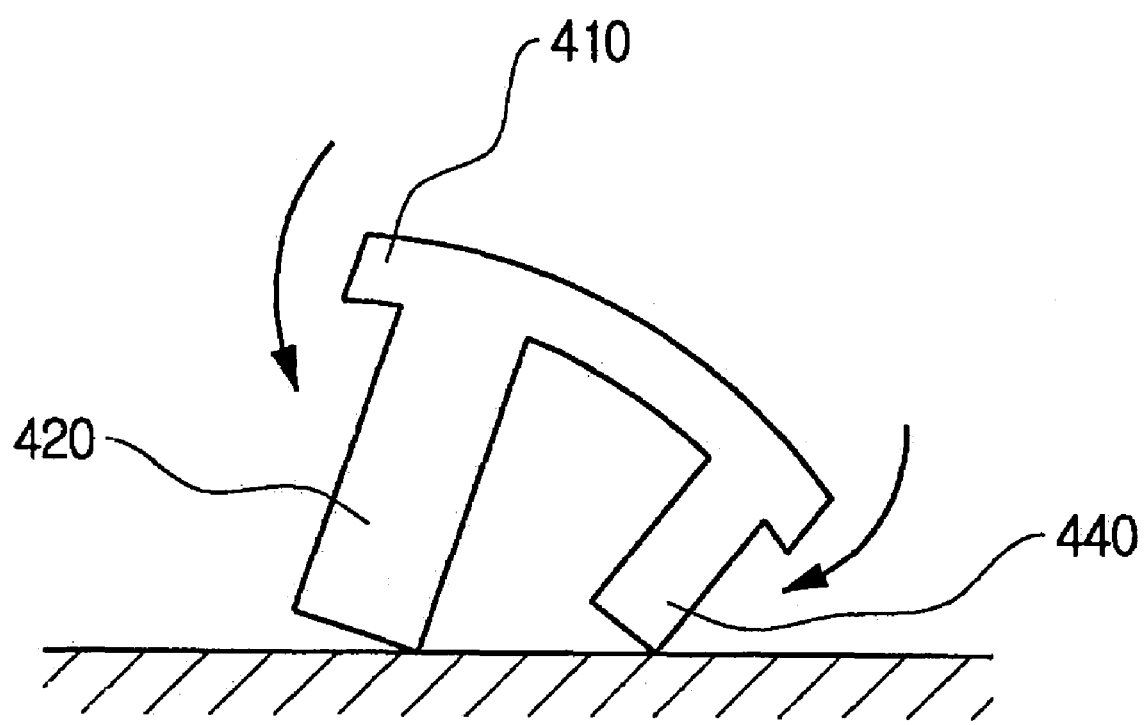
FIG. 20 is a side view showing a movement state of the moving actuator in FIG. 18.

FIGS. 19 and 20 are schematic views illustrating a movement state of the moving actuator 400 of FIG. 18. In FIG. 19, the moving actuator 400 becomes to be in a state that the body 410 is inclined to the bottom due to the length difference. In this state, when the muscular cell transplanted under the body 410 repeats contraction or relaxation, as shown in FIG. 20, the body 410 is twisted in an arrow direction so that bending or unbending thereof are repeated. As the body 410 is repeatedly bent and unbent, the legs 440 of the body advance on the bottom to thus advance the actuator 400.

Figure 21:
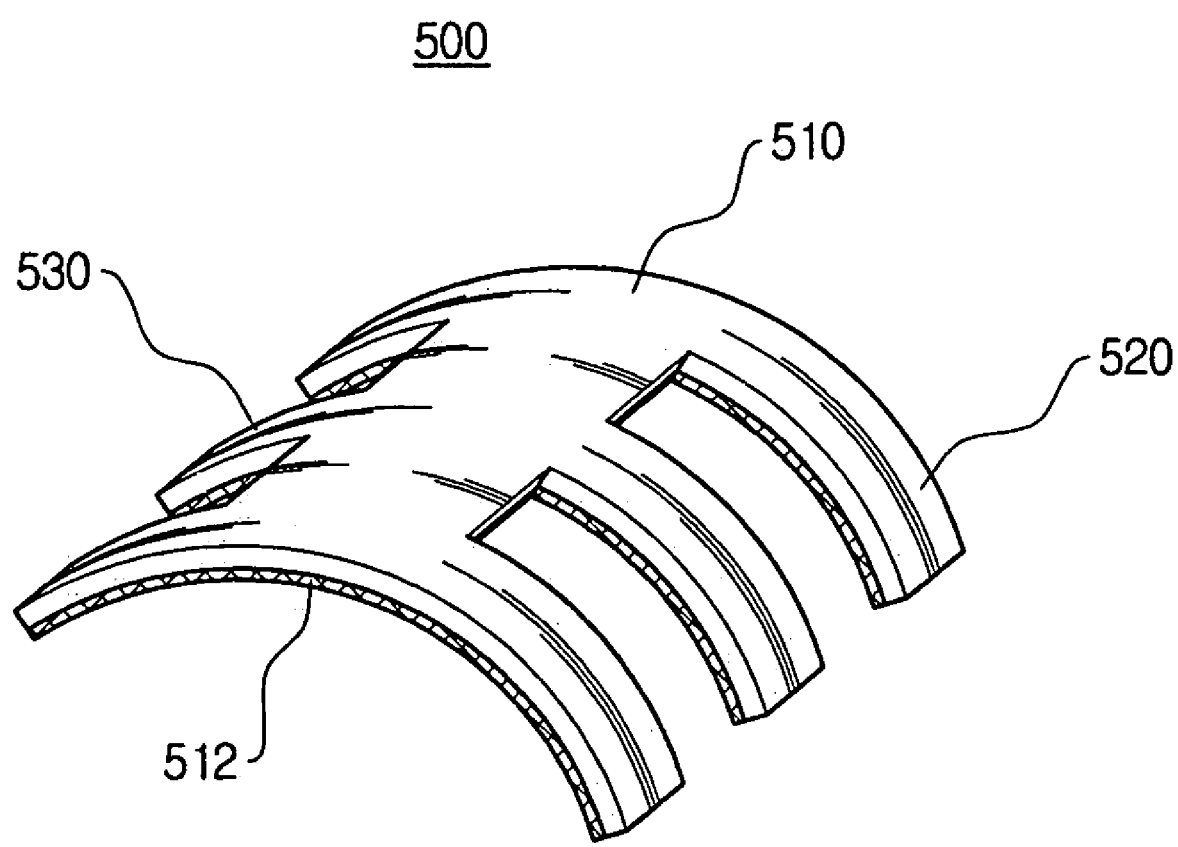
FIG. 21 is a perspective view of a moving actuator having a plurality of cantilevers.

FIG. 21 shows a moving actuator 500 comprising a plurality of the cantilevers in FIG. 15.

Referring to FIG. 21, the actuator of this embodiment includes a rectangular body 510, and a plurality of cantilevers 520 and 530 extending from both sides of the body 510. Herein, the cantilevers 520 and 530 have different length. The right-side cantilevers 520 in FIG. 21 have a longer length than the left-side cantilevers 530. The difference between cantilevers is a source of moving the actuator, and is described later in detail. The muscular cell is transplanted onto the bottom of the body 510 and the cantilevers 520 and 530.

Figure 22:
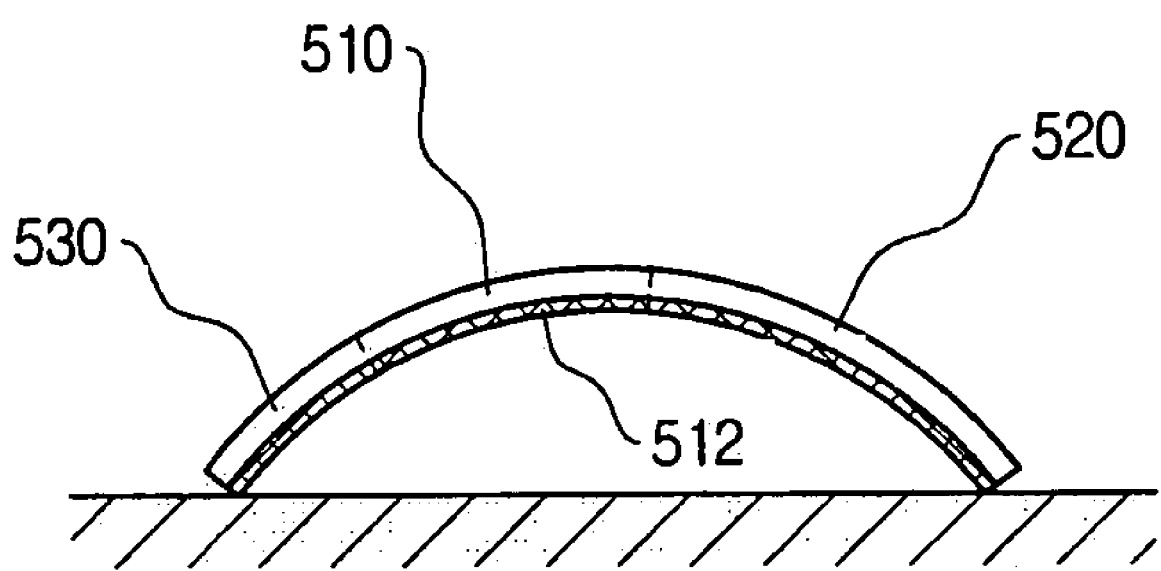
FIG. 22 is a side view showing a state that the moving actuator in FIG. 21 is curved to a bottom.
Figure 23:
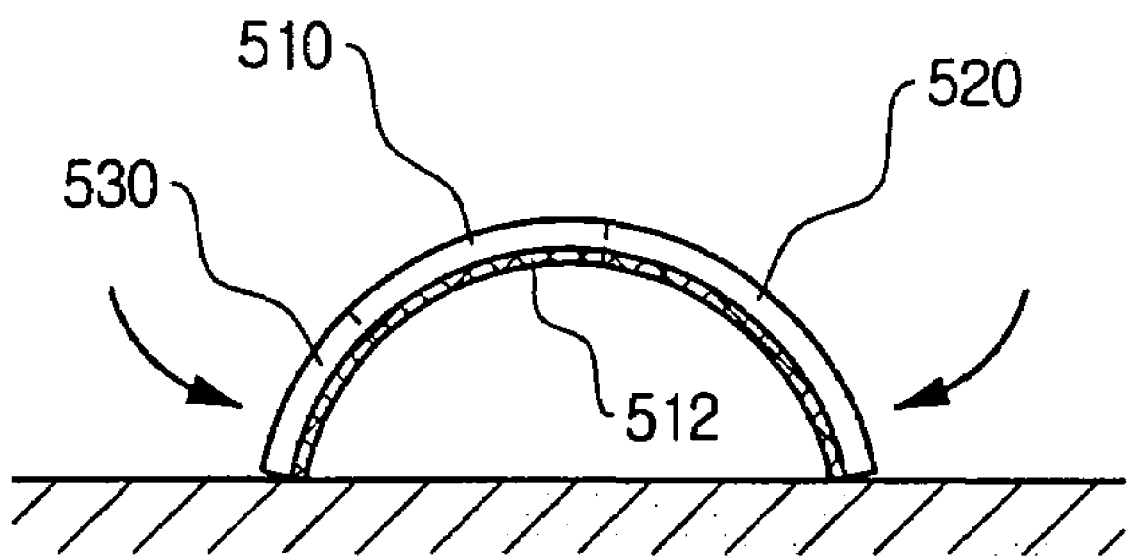
FIG. 23 is a side view showing a movement state of the moving actuator in FIG. 21.

FIGS. 22 and 23 are schematic views illustrating a movement state of the moving actuator 500 of FIG. 21. In FIG. 22, the moving actuator 500 becomes to be in a state that the body 510 and the cantilevers 520 and 530 are curved to the bottom. In this state, when the muscular cell transplanted under the body 510 and the cantilevers 520 and 530 repeats contraction or relaxation, as shown in FIG. 23, the body 510 and the cantilevers 520 and 530 are twisted in an arrow direction so that bending or unbending thereof are repeated. As the body 510 and cantilevers 520 and 530 are repeatedly bent and unbent, the cantilevers 520 and 530 of the body 510 advance on the bottom to thus advance the actuator 500.

The bio actuator manufactured by the above process can be made in various forms according to a purpose desired to use, and does not require a separate external energy source because it operates on glucose after introduced into the human body.

In addition, the muscular cell used in the bio actuator may be one or more.

In addition, since the molding aligning apparatus of the present invention can implement a molding process for 3-dimensional shape member, a micro-fluidic product such as a micro mixer, a micro valve, or a micro pump can be manufactured by the present invention.

In addition, the molding aligning apparatus of the present invention can implement an align process in wafer unit so that it can be used in glass-to-glass thermal bonding or epoxy based wafer unit bonding as well as molding apparatus.

According to a 3-dimensional micro molding aligning apparatus of the present invention, an actuator is molded using upper and lower half molds to thus easily manufacture a complicated shaped actuator.

In addition, according to a 3-dimensional micro molding aligning apparatus of the present invention, a lower half mold can be controlled in alignment with an upper half mold by moving it in X or Y direction, or rotating it about an Z-axis, using an aligner unit, to thus manufacture a precise actuator.

According to a bio actuator and a manufacturing method thereof of the present invention, an actuator is manufactured using a harmless material compatible with the human body so that it can be introduced into the human body without a rejection and be used for the purpose of treatment such as removal of cancer cells, and that it does not require a separate external energy source because the actuator operates on glucose in the human body, thereby manufacturing a compact actuator.

In addition, a muscular cell can be cultivated in a bio actuator body, and selectively bound and effectively removed using a collagen and a cleaning solution, so that it is possible to achieve mass production.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A 3-dimensional micro molding aligning apparatus for 3-dimensionally molding a bio actuator body, the apparatus comprising: a base having thereon a plurality of support legs; a mold plate unit supported by the support legs and having upper and lower half molds corresponding to an outer contour of the bio actuator and installed opposite to each other and having one or more viewing windows for observing the aligned state of the upper and lower half molds; an aligner unit positioned on the base and aligning the lower half mold with the upper half mold; and a clamp unit selectively fixed to the upper portion of the mold plate unit and pressing the upper half mold of the mold plate unit toward the lower half mold.

2. The apparatus as claimed in claim 1, wherein the mold plate unit comprises: a lower mold plate supported by the plurality of support legs installed on the base and having a center through-hole; a middle mold plate movably positioned above the lower mold plate and having thereon a fixture portion for fixing the lower half mold; and an upper mold plate positioned above the middle mold plate and having at its under surface a fixture portion for fixing the upper half mold.

3. The apparatus as claimed in claim 2, wherein the aligner unit comprises: a connection member connected with the middle mold plate through the through-hole of the lower mold plate to interwork therewith; a X-directional aligner for moving the connection member in X-direction; a Y-directional aligner for moving the connection member in Y-direction; and a rotary aligner for rotating the connection member about an Z-axis, whereby the lower half mold is aligned with the upper half mold.

4. The apparatus as claimed in claim 3, wherein the upper mold plate has the viewing windows, and the upper half mold is made of glass.

5. The apparatus as claimed in claim 2, wherein the clamp unit comprises: a body portion in length; a pair of pivot legs installed on both ends of the body portion and having extensions extending vertically from the distal end thereof for supporting the mold plate trait; and a pressing bolt for pressing the upper mold plate toward the middle and lower mold plates while passing through the body portion, thereby pressing the upper half mold toward the lower half mold.

6. The apparatus as claimed in claim 5, wherein an anti-deformation member is installed at art end of the pressing bolt to be brought into contact with the upper mold plate so as to prevent the deformation of the upper mold plate when the upper mold plate is pressed with the pressing bolt.

7. A method for manufacturing a bio actuator transplanted with a muscular cell, the method comprising the steps of: 3-dimensionally forming an actuator body with polymer using the micro molding aligning apparatus as claimed in claim 1; and transplanting and cultivating the muscular cell onto the actuator body.

8. The method as claimed in claim 7, wherein the step of forming the actuator body comprises: preparing the upper and lower half molds corresponding to art outer contour of the actuator; installing, on the mold plate unit, the upper and lower half molds opposite to each other and placing a mass of polymer above the lower haft mold; aligning the lower half mold with the upper half mold using the aligner unit; pressing the mold plate unit using the clamp unit; solidifying the polymer; and removing the solidified polymer.

9. The method as claimed in claim 8, wherein the polymer is polydimethylsiloxane (PDMS).

10. The method as claimed in claim 8, wherein the step of forming the actuator body further, comprises coating onto the polymer fibronectin compatible with the muscular cell and having a great binding force for the polymer.

11. The method as claimed in claim 8, wherein the lower half mold is composed of a silicon wafer, and a release accelerant solution is coated onto the lower half mold to form silane group, or $C_4F_8$ is coated in plasma onto the silicon wafer using deep RIE for the actuator body to be easily removed from the lower half mold.

12. The method as claimed in claim 11, wherein the release accelerant solution is tridecafluro-1,1,2,2-tetrahydrooctyl-1-trichlorosilane.

13. The method as claimed in claim 10, wherein the fibronectin is coated onto the polymer after OH group is formed using $O_2$ plasma.

14. The method as claimed in claim 7, wherein the step of transplanting and cultivating the muscular cell on the actuator body is implemented without transplanting the externally cultivated muscular cell onto the actuator body so that the muscular cell is transplanted onto the actuator body in a state that the actuator body is immersed into a culture solution, and the actuator body is operated in the culture solution.

15. The method as claimed in claim 14, wherein the culture solution contains glucose.

16. The method as claimed in claim 7,
wherein the step of transplanting and cultivating the muscular cell comprises: setting the actuator body in a culture vessel; and transplanting the muscular cell onto the actuator body in the culture vessel filled with a culture solution and cultivating the same.

17. The method as claimed in claim 16, wherein the culture solution contains glucose.

18. The method as claimed in claim 16, wherein the step of setting the actuator body in the culture vessel comprises:
   applying to the culture vessel a polymer in thickness having a small binding force for the muscular cell, to form a polymer substrate; and
   positioning the actuator body above the polymer substrate.

19. The method as claimed in claim 18, wherein the polymer is PDMS.

20. The method as claimed in claim 16, wherein the step of transplanting and cultivating the muscular cell is implemented such that the muscular cell optionally introduced into the culture vessel is bound to the actuator body coated with the fibronectin compatible with the muscular cell.

21. The method as claimed in claim 20, wherein the step of transplanting and cultivating the muscular cell is implemented such that after the cultivation of the muscular cell, the actuator body and the polymer substrate are cleaned using a Hanks' balanced salt solution (HBSS) to remove the muscular Cell from the polymer substrate.

22. The apparatus as claimed in claim 2, wherein the lower half mold is detachably fixed to the fixture portion of the middle mold plate, and the upper half mold is detachably fixed to the fixture portion of the upper mold plate.

* * * * *